United States Patent [19]
Cone et al.

[11] Patent Number: 5,532,347
[45] Date of Patent: Jul. 2, 1996

[54] DNA ENCODING α MELANOCYTE STIMULATING HORMONE RECEPTOR

[75] Inventors: Roger D. Cone, Oregon City; Kathleen G. Mountjoy, Portland, both of Oreg.

[73] Assignee: State of Oregon, Acting by and Through the Oregon State Board of Higher Education on behalf of the Oregon Health Sciences University, a non-profit organization, Potland, Oreg.

[21] Appl. No.: 866,979

[22] Filed: Apr. 10, 1992

[51] Int. Cl.$^6$ .......................... C07H 21/04; C07K 14/72; C12N 5/10; C12N 15/12; C12N 15/63
[52] U.S. Cl. .................. 536/23.5; 435/320.1; 435/240.1; 435/69.1; 935/9; 935/66; 530/351; 530/312
[58] Field of Search ................. 536/23.5, 24.31; 435/320.1; 514/8; 530/387.1, 395, 399

[56] References Cited

PUBLICATIONS

J. E. Gerst et al. Mol. Pharmacol. 31:81 1987.
F. Libert et al. Science 244:569 1989.
Q.-Y Zhou et al. Nature 347:76–80 Sep. 1990.
Y. Masu et al. Nature 329:836 1987.
Hanneman et al., in Peptide Hormone as Prohormones, G. Martinez, ed. (Ellis Horwood Ltd.: Chichester, UK) pp. 53–82.
DeWied & Jolles, 1982, Physiol. Rev. 62:976–1059.
Shimuze, 1985, Yale J. Biol. Med. 58:561–570.
Tatro & Reichlin, 1987, Endocrinology 121: 1900–1907.
Solca et al., 1989, J. Biol. Chem. 264: 14277–14280.
Siegrist et al., 1991 J. Receptor Res. 11: 323–331.

*Primary Examiner*—Garnette D. Draper
*Assistant Examiner*—L. Spector
*Attorney, Agent, or Firm*—Banner & Allegretti, Ltd.

[57] ABSTRACT

The present invention relates to a mammalian melanocyte stimulating hormone receptor. The invention is directed toward the isolation, characterization and pharmacological use of mammalian melanocyte stimulating hormone receptor, the gene corresponding to this receptor, a recombinant eukaryotic expression construct capable of expressing a mammalian melanocyte stimulating hormone receptor in cultures of transformed eukaryotic cells and such cultures of transformed eukaryotic cells that synthesize mammalian melanocyte stimulating hormone receptor. The invention also provides methods for screening $MSH^R$ agonists and antagonists in vitro using preparations of receptor from such cultures of eukaryotic cells transformed with a recombinant eukaryotic expression construct comprising the $MSH^R$ receptor gene. The invention specifically provides human and mouse $MSH^R$ genes.

8 Claims, 12 Drawing Sheets

FIG. 1A

```
        10          20          30          40          50          60          70
TTCCTGACAA GACTATGTCC ACTCAGGAGC CCCAGAAGAG TCTTCTGGGT TCTCTCAACT CCAATGCCAC 80          90         100         110         120         130         140
CTCTCACCTT GGACTGGCCA CCAACCAGTC AGAGCCTTGG TGCCTGTATG TGTCCATCCC AGATGGCCTC 150         160         170         180         190         200         210
TTCCTCAGCC TAGGGCTGGT GAGTCTGGTG GAGAATGTGC TGGTTGTGAT AGCCATCACC AAAAACCGCA 220         230         240         250         260         270         280
ACCTGCACTC GCCCATGTAT TACTTCATCT GCTGCCTGGC CCTGTCTGAC CTGATGGTAA GTGTCAGCAT 290         300         310         320         330         340         350
CGTGCTGGAG ACTACTATCA TCCTGCTGCT GGAGGTGGGC ATCCTGGTGG CCAGAGTGGC TTTGGTGCAG 360         370         380         390         400         410         420
CAGCTGGACA ACCTCATTGA CGTGCTCATC TGTGGCTCCA TGGTGTCCAG TCTCTGCTTC CTGGGCATCA 430         440         450         460         470         480         490
TTGCTATAGA CCGCTACATC TCCATCTTCT ATGCGCTGCG TTATCACAGC ATCGTGACGC TGCCCAGAGC 500         510         520         530         540         550         560
ACGACGGGCT GTCGTGGGCA TCTGGATGGT CAGCATCGTC TCCAGCACCC TCTTTATCAC CTACTACAAG
```

FIG. 1B

```
 570        580        590        600        610        620        630
CACACAGCCG TTCTGCTCTG CCTCGTCACT TTCTTTCTAG CCATGCTGGC ACTCATGGCG ATTCTGTATG 640        650        660        670        680        690        700
CCCACATGTT CACGAGAGCG TGCCAGCACG TCCAGGGCAT TGCCCAGCTC CACAAAAGGC GGCGGTCCAT 710        720        730        740        750        760        770
CCGCCAAGGC TTCTGCCTCA AGGGTGCTGC CACCCTTACT ATCCTTCTGG GGATTTTCTT CCTGTGCTGG 780        790        800        810        820        830        840
GGCCCCTTCT TCCTGCATCT CTTGCTCATC GTCCTCTGCC CTCAGCACCC CACCTGCAGC TGCATCTTCA 850        860        870        880        890        900        910
AGAACTTCAA CCTCTTCCTC CTCCCTCATCG TCCTCAGCTC CACTGTTGAC CCCCTCATCT ATGCTTTCCG 920        930        940        950        960        970        980
CAGCCAGGAG CTCCGCATGA CACTCAAGGA GGTGCTGCTG TGCTCCTGGT GATCAGAGGG CGCTGGGCAG 990       1000       1010       1020       1030       1040       1050
AGGGTGACAG TGATATCCAG TGGCCTGCAT CTGTGAGACC ACAGGTACTC ATCCCTTCCT GATCTCCATT 1060       1070       1080       1090       1100       1110       1120
TGTCTAAGGG TCGACAGGAT GAGCTTTAAA ATAGAAACCC AGAGTGCCTG GGGCCAGGAG AAAGGGTAAC
```

FIG. 1C

```
     1130       1140       1150       1160       1170       1180       1190
TGTGACTGCA GGGCTCACCC AGGGCAGCTA CGGGAAGTGG AGGAGACAGG GATGGGAACT CTAGCCCTGA 1200       1210       1220       1230       1240       1250       1260
GCAAGGGTCA GACCACAGGC TCCTGAAGAG CTTCACCTCT CCCCACCTAC AGGCAACTCC TGCTCAAGCC
```

FIG. 1D

```
         10         20         30         40         50         60         70
CCCGCATGTG GCCGCCCTCA ATGGAGGGCT CTGAGAACGA CTTTTAAAAC GCAGAGAAAA AGCTCCATTC
         80         90        100        110        120        130        140
TTCCCAGACC TCAGCGCAGC CCTGGCCCAG GAAGGCAGGA GACAGAGGCC AGGACGGTCC AGAGGTGTCG
        150        160        170        180        190        200        210
AAATGTCCTG GGAACCTCAG CAGCAGCCAC CAGGGAAGAG GCAGGGAGGG AGCTGAGGAC CAGGCTTGGT
        220        230        240        250        260        270        280
TGTGAGAATC CCTGACCCCA GGCGGGTTGAT GCCAGGAGGT GTCTGGACTG GCTGCGCCAT GCCTGGGCTG
        290        300        310        320        330        340        350
ACCTGTCCAG CCAGGCAGAG GGTGTGAGGG CAGATCTGGG GGTGCCCAGA TGGAAGGAGG CAGGCATGCG
        360        370        380        390        400        410        420
GACACCCAAG GCCCCCTGGC AGCACCATGA ACTAAGCAGG ACACCTGGAG GGGAAGAACT CTGGGGACCT
```

FIG. 1E

| 430 | 440 | 450 | 460 | 470 | 480 | 490 |
|---|---|---|---|---|---|---|
| GGAGGCCTCC | AACGACTCCT | TCCTGCTTCC | TGGACAGGAC | TATGGCTGTC | CAGGGATCCC | AGAGAAGACT |

| 500 | 510 | 520 | 530 | 540 | 550 | 560 |
|---|---|---|---|---|---|---|
| TCTGGGCTCC | CTCAACTCCA | CCCCACAGC | CATCCCCCAG | CTGGGGCTGG | CTGCCAACCA | GACAGGAGCC |

| 570 | 580 | 590 | 600 | 610 | 620 | 630 |
|---|---|---|---|---|---|---|
| CGGTGCCTGG | AGGTGTCCAT | CTCTGACGGG | CTCTTCCTCA | GCCTGGGGCT | GGTGAGCTTC | GTGGAGAACG |

| 640 | 650 | 660 | 670 | 680 | 690 | 700 |
|---|---|---|---|---|---|---|
| CGCTGGTGGT | GCCCACCATC | GCCAAGAACC | GGAACCTGCA | CTCACCCATC | TACTGCTTCA | TCTGCTGCCT |

| 710 | 720 | 730 | 740 | 750 | 760 | 770 |
|---|---|---|---|---|---|---|
| GGCCTTGTCG | GACCTGCTGG | TGAGCGGGAC | GAACGTGCTG | GAGACGGCCG | TCATCCTCCT | GCTGGAGGCC |

| 780 | 790 | 800 | 810 | 820 | 830 | 840 |
|---|---|---|---|---|---|---|
| GGTGCACTGG | TGGCCCGGGC | TGCGGTGCTG | CAGCAGCTGG | ACAATGTCAT | TGACGTGATC | ACCTGCAGCT |

| 850 | 860 | 870 | 880 | 890 | 900 | 910 |
|---|---|---|---|---|---|---|
| CCATGCTGTC | CAGCCTCTGC | TTCCTGGGCG | CCATCGCCGT | GGACCGCTAC | ATCTCCATCT | TCTACGCACT |

| 920 | 930 | 940 | 950 | 960 | 970 | 980 |
|---|---|---|---|---|---|---|
| GCGCTACCAC | AGCATCGTGA | CCCTGCCGCG | GGCGCCGCGA | GCCGTTGCGG | CCATCTGGGT | GGCCAGTGTC |

FIG. 1F

```
 990        1000       1010       1020       1030       1040       1050
GTCTTCAGCA CGCTCTTCAT CGCCTACTAC CACCACGTGG CCGTCCTGCT GTGCCTCGTG CTCTTCTTCC 1060       1070       1080       1090       1100       1110       1120
TGGCTATGCT GGTGCTCATG GCCGTGCTGT ACGTCCACAT GCTGGCCCGG GCCTGCCAGC ACGCCCAGGG 1130       1140       1150       1160       1170       1180       1190
CATCGCCCGG CTCCACAAGA GGCAGCGCCC GGTCCACCAG GGCTTTGGCC TTAAAGGCGC TGTCACCCTC 1200       1210       1220       1230       1240       1250       1260
ACCATCCTGC TGGGCATTTT CTTCCTCTGC TCGGGCCCCT TCTTCCTGCA TCTCACACTC ATCGTCCCTCT 1270       1280       1290       1300       1310       1320       1330
GCCCGAGCA CCCCACGTGC GGCTGCATCT TCAAGAACTT CAACCTCTTT CTCGCCCCTCA TCATCTGCAA 1340       1350       1360       1370       1380       1390       1400
TGCCATCATC GACCCCCTCA TCTACGCCTT CCACAGCCAG GAGCTCCGCA GCACGCTCAA GGAGGTGCTG 1410       1420       1430       1440       1450       1460       1470
ACATGCTCCT GGTGAGGCCG CTGCACGCGC TTTAAGTGTG CTGGGCAGAG GGAGGTGGTG ATATTGTGGT 1480       1490       1500       1510       1520       1530       1540
CTGGTTCCCTG TGTGACCCTG GGCAGTTCCT TACCTCCCTG GTCCCCGTTT GTCAAAGACG ATGGACTAAA
```

FIG. 1G

```
         1550       1560       1570       1580       1590       1600       1610
TGATCTCTGA AAGTGTTGAA GCGCGGACCC TTCTGGGCAG GGAGGGGTCC TGCAAAACTC CAGGCAGGAC 1620       1630
TTCTCACCAG CAGTCGTGGG AAC
```

FIG. 2A

```
MOUSE MSH-R                                              mstQepQkaLvGSLNSnaTah--    21
HUMAN MHS-R                                              mavQgsQrrLlGSLNStpTaipq    23
HUMAN ACTH-R                                                         mkhiinsye      9
RAT CANNAB.     m-(101)-----------------------------------------------------      102

I
MOUSE MSH-R     LGLATNQsepwCLyVSIPDGLFLSLGLVSLVENvLVViAItKNRNLHcPMYyFICCLALSD       82
HUMAN MHS-R     -LGLAaNQtgarCLeVSIsDGLFLSLGLVSLVENaLVVatIaKNRNLHsPMYCFICCLALSD      84
HUMAN ACTH-R    ninnTarnnadCprVvlPeeiFfTisiVgvlENlivllAvfKNkNLqaPMYfFICsLAisD       70
RAT CANNAB.     ---------------------L--LtLg----VLENLLVL--I---R-L--P-Y-FI-SLA---D  163

II
                                                        III
MOUSE MSH-R     LmVSvsiVLETtiLLLLEvGiLVARvAlvQQLDNlIDVliCgSMvSSLCFLGiIAiDRYIS      143
HUMAN MHS-R     -LLVSgtnVLEtavILLLEaGaLVARaAvlQQLDNvIDVitCsSMLSSLCFLGaIAvDRYIS     145
HUMAN ACTH-R    mLgSlykiLEnilliLrnmGyLkpRgsfettaDdiIDslfvlSiLgSifsLsvIAaDRYit      131
RAT CANNAB.     LLGSV--V----------------F--------------V-----GSLF-L---AIDRYIS     224
                                II
```

FIG. 2B

```
                        IV                                                         V
MOUSE MSH-R    IFYALRYHSIVTLPRArRAVvgIWmvSivSSTLFItyYkHtAVLLCLVtFFLAMLaIMAiL   204
HUMAN MHS-R    -IFYALRYHSIVTLPRArRAVaaIWvaSvvfSTLFIayYdHVAVLLCLVvFFLAMLVMAVL   206
HUMAN ACTH-R   IFhALRYHSIVTmrRtvvvltvIWTfctgtgitmvifshHVptvitftslFplMLVfilcL   192
RAT CANNAB.    I----L-Y---IVT-P-AVVA-----WT--IV---L------------FPL----L--    285

V                                                VI
MOUSE MSH-R    YaHMFtRACQHvQGIAqLHKRQRsirQGFsLKGAaTLTILLGIFFLCWGPFFLHLLLIVLC   264
HUMAN MHS-R    -YVHMLaRACQHaQGIARLHKRQRpvhQGFgLKGAVTLTILLGIFFLCWGPFFLHLtLIVLC   266
HUMAN ACTH-R   -YVHMF-----liARsHtRkistlpranmKGAiTLTILLGvFifCWaPFvLHvLLmtfC      245
RAT CANNAB.    -----------(31)----RP----R----A-TL---L-V-I-CWGP-------        373

VII
MOUSE MSH-R    PqHPTCaCIFKNFNLFLlLivlsstvDPLIYAFRSQELRmTLKEVLlCS--W            317
HUMAN MHS-R    -PeHPTCgCIFKNFNLFLaLiiCNAiIDPLIYAFhSQELRrTLKeVLtCS--W            316
HUMAN ACTH-R   -PsnPyCaCymslFgvngMLimCNAvIDPfIYAFRSpKLRdafKkmifCSryW            297
RAT CANNAB.    -------I---F----ML--LNSTV-P-IYA-RS--LR-AF--M-F-S---(56)         483
```

DNA ENCODING α MELANOCYTE STIMULATING HORMONE RECEPTOR

This invention was made with government support under 1R01DK41921-03, 1R01DK43859-01, and 1P01DK44239-10A1 by the National Institutes of Health. The government has certain rights in the invention.

BACKGROUND OF THE INVENTION

1. Field of the Invention

This invention relates to melanocyte stimulating hormone receptors from mammalian species and the genes corresponding to such receptors. Specifically, the invention relates to the isolation, cloning and sequencing of a human melanocyte stimulating hormone receptor gene. The invention also relates to the isolation, cloning and sequencing of a mouse melanocyte stimulating hormone receptor gene. The invention relates to the construction of eukaryotic recombinant expression constructs capable of expressing these melanocyte stimulating hormone receptors in cultures of transformed eukaryotic cells, and the production of the melanocyte stimulating hormone receptor in such cultures. The invention relates to the use of such cultures of transformed eukaryotic cells to produce homogeneous compositions of such melanocyte stimulating hormone receptors. The invention also provides cultures of such cells producing melanocyte stimulating hormone receptor for the characterization of novel and useful drugs. Antibodies against and epitopes of these melanocyte stimulating hormone receptor proteins are also provided by the invention.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well understood roles in control of melanocyte and adrenocortical function, respectively. Both of these hormones, however, are found in a variety of forms with unknown functions. The melanocortin peptides also have a diverse array of biological activities in other tissues, including the brain, and immune system, and bind to specific receptors there with a distinct pharmacology [see, Hanneman et al., in *Peptide Hormone as Prohormones*, G. Martinez, ed. (Ellis Horwood Ltd.: Chichester, UK) pp. 53–82; DeWied & Jolles, 1982, Physiol. Rev. 62: 976–1059 for reviews].

A complete understanding of these peptides and their diverse biological activities requires the isolation and characterization of their corresponding receptors. Some biochemical studies have been reported on the prior art.

Shimuze, 1985, Yale J. Biol. Med. 58: 561–570 discusses the physiology of melanocyte stimulating hormone.

Tatro & Reichlin, 1987, Endocrinology 121: 1900–1907 disclose that MSH receptors are widely distributed in rodent tissues.

Solca et al., 1989, J. Biol. Chem. 264: 14277–14280 disclose the molecular weight characterization of mouse and human MSH receptors linked to radioactively and photoaffinity labeled MSH analogues.

Siegrist et al., 1991, J. Receptor Res. 11: 323–331 disclose the quantification of receptors on mouse melanoma tissue by receptor autoradiography.

The present invention comprises a human melanocyte stimulating hormone receptor gene, the nucleotide sequence of this gene and the deduced amino acid sequence of its cognate protein, a homogeneous composition of the melanocyte stimulating hormone receptor, nucleic acid hybridization probes and a method for determining the tissue distribution of expression of the gene, a recombinant expression construct capable of expressing the gene in cultures of transformed eukaryotic cells, and such cultures of transformed eukaryotic cells useful in the characterization of novel and useful drugs. The present invention also comprises the homologue of the human melanocyte stimulating hormone receptor gene from the mouse.

DESCRIPTION OF THE DRAWINGS

FIGS. 1a and 1b illustrate the nucleotide sequence of the mouse (SEQ ID NO:3) and human (SEQ ID NO:5) melanocyte stimulating hormone receptor, respectively.

FIG. 2 presents an amino acid sequence comparison between the mouse and human melanocyte stimulating hormone receptor proteins.

SUMMARY OF THE INVENTION

Figure 3:
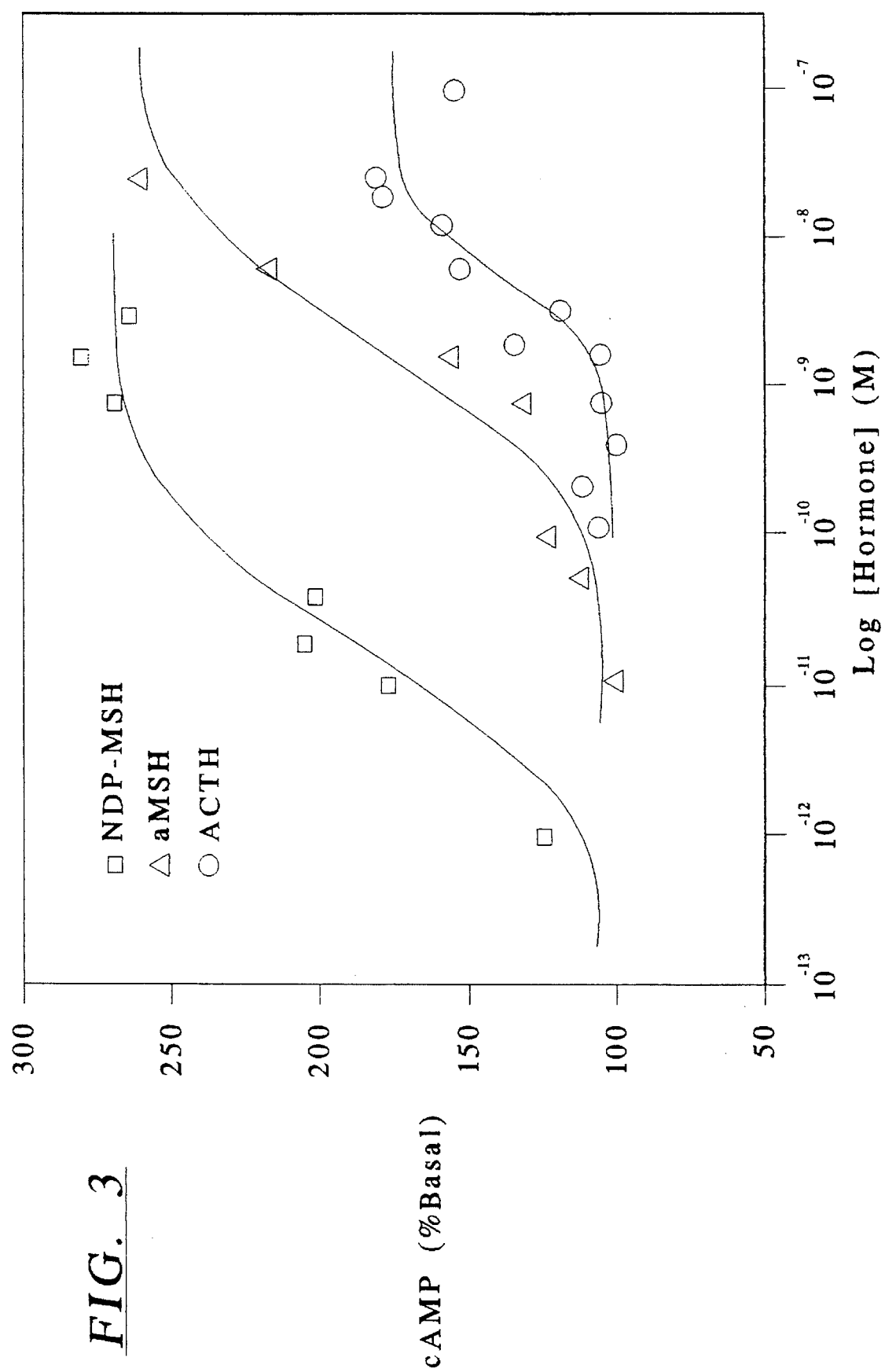
FIG. 3 illustrates binding of melanocyte stimulating hormone receptor agonists to mouse melanocyte stimulating hormone receptor expressed in human 293 cells.

The present invention relates to the cloning, expression and functional characterization of mammalian melanocyte stimulating hormone receptor (MSH®) genes. The invention comprises the nucleotide sequence of these genes encoding the mammalian MSH®s and the deduced amino acid sequences of the cognate proteins, as well as tissue distribution patterns of expression of these genes.

In particular, the present invention is directed toward the isolation, characterization and pharmacological use of the human MSH®, the gene corresponding to this receptor, a nucleic acid hybridization probe comprising DNA sequences of the human MSH®, a recombinant eukaryotic expression construct capable of expressing the human MSH® in cultures of transformed eukaryotic cells and such cultures of transformed eukaryotic cells that synthesize the human MSH®, a homogeneous composition of the human MSH®, and antibodies against and epitopes of the human MSH®.

The present invention is also directed toward the isolation, characterization and pharmacological use of the mouse MSH®, the gene corresponding to this receptor, a nucleic acid hybridization probe comprising DNA sequences of the mouse MSH®, a recombinant eukaryotic expression construct capable of expressing the mouse MSH® in cultures of transformed eukaryotic cells and such cultures of transformed eukaryotic cells that synthesize the mouse MSH®, a homogeneous composition of the mouse MSH®, and antibodies against and epitopes of the mouse MSH®.

It is an object of the invention to provide a nucleotide sequence encoding a mammalian MSH®. In a preferred embodiment of the invention, the nucleotide sequence encodes the human MSH®. In another preferred embodiment, the nucleotide sequence encodes the mouse MSH®.

The present invention includes a nucleotide sequence encoding a human MSH® receptor derived from a DNA molecule isolated from a human genomic library (SEQ ID NO:5). In this embodiment of the invention, the nucleotide sequence includes 1635 nucleotides of the human MSH® gene comprising 953 nucleotides of coding sequence, 462 nucleotides of 5' untranslated sequence and 220 nucleotides of 3' untranslated sequence.

The present invention also includes a nucleotide sequence encoding a mouse MSH® derived from a cDNA molecule isolated from a cDNA library constructed with RNA from mouse Cloudman melanoma cells (SEQ ID NO:3). In this embodiment of the invention, the nucleotide sequence includes 1260 nucleotides of the mouse MSH® gene comprising 947 nucleotides of coding sequence, 15 nucleotides of 5' untranslated sequence and 298 nucleotides of 3' untranslated sequence.

The invention includes nucleotide sequences of mammalian MSH®s, most preferably mouse and human MSH®s (SEQ ID NOs:3&5), and includes allelic variations of these nucleotide sequences and the corresponding MSH® molecule, either naturally occurring or the product of in vitro chemical or genetic modification, each such variant having essentially the same nucleotide sequence as the nucleotide sequence of the corresponding MSH® disclosed herein, wherein the resulting MSH® molecule has substantially the same biological properties as the MSH® molecule corresponding to the nucleotide sequence described herein. The term "substantially homologous to" as used in this invention encompasses such allelic variability as described in this paragraph.

The invention also includes a predicted amino acid sequence for the mouse (SEQ ID NO:4) and human (SEQ ID NO:6) MSH® deduced from the nucleotide sequence comprising the complete coding sequence of the mouse (SEQ ID NO:3) and human (SEQ ID NO:5) MSH® gene as described herein.

In another aspect, the invention comprises a homogeneous composition of a 35.3 kilodalton mouse MSH® or derivative thereof, wherein the amino acid sequence of the MSH® or derivative thereof comprises the mouse MSH-R sequence shown in FIG. 2 (SEQ ID NO:4).

In another aspect, the invention comprises a homogeneous composition of a 34.7 kilodalton human MSH® or derivative thereof, wherein the amino acid sequence of the MSH® or derivative thereof comprises the human MSH-R sequence shown in FIG. 2 (SEQ ID NO:6).

This invention provides both nucleotide and amino acid probes derived from these sequences. The invention includes probes isolated from either cDNA or genomic DNA clones, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide sequences of mammalian MSH®, preferably the mouse or human MSH®, for use as nucleic acid hybridization probes to determine the pattern, amount and extent of expression of this receptor in various tissues of mammals, including humans. It is also an object of the present invention to provide nucleic acid hybridization probes derived from the sequences of the mouse or human MSH® to be used for the detection and diagnosis of genetic diseases. It is an object of this invention to provide nucleic acid hybridization probes derived from the DNA sequences of the mouse or human MSH® to be used for the detection of novel related receptor genes.

The present invention also includes synthetic peptides made using the nucleotide sequence information comprising cDNA or genomic clone embodiments of the invention. The invention includes either naturally occurring or synthetic peptides which may be used as antigens for the production of MSH®-specific antibodies, or used for competitors of the MSH® molecule for drug binding, or to be used for the production of inhibitors of the binding of agonists or antagonists or analogues thereof to MSH® molecule.

The present invention also provides antibodies against and epitopes of mammalian MSH®s, preferably mouse or human MSH® proteins. It is an object of the present invention to provide antibodies that is immunologically reactive to a mammalian MSH® protein. It is a particular object of the invention to provide a monoclonal antibodies to mammalian MSH® protein, most preferably mouse or human MSH® protein.

It is also an object of the present invention to provide a hybridoma cell line that produces such an antibody. It is a particular object of the invention to provide a hybridoma cell line that is the result of fusion between a non-immunoglobulin producing mouse myeloma cell line and spleen cells derived from a mouse immunized with a human cell line which expresses MSH® antigen. The present invention also provides a hybridoma cell line that produces such an antibody, and that can be injected into a living mouse to provide an ascites fluid from the mouse that is comprised of such an antibody.

The present invention also provides a pharmaceutical composition comprising a therapeutically effective amount of a monoclonal antibody that is immunologically reactive to a mammalian MSH®, preferably a mouse or human MSH®, and in a pharmaceutically acceptable carrier.

It is a further object of the present invention to provide an epitope of a mammalian MSH® protein wherein the epitope is immunologically reactive to an antibody specific for the mammalian MSH®. In preferred embodiments, the epitope is derived from mouse of human MSH® protein.

It is another object of the invention to provide a chimeric antibody that is immunologically reactive to a mammalian MSH® protein. In a preferred embodiment, the chimeric antibody is a monoclonal antibody. In a preferred embodiment, the MSH® is a mouse or human MSH®.

The present invention provides a recombinant expression construct comprising the nucleotide sequence of a mammalian MSH®, preferably the mouse or human MSH® and sequences sufficient to direct the synthesis of mouse or human MSH® in cultures of transformed eukaryotic cells. In a preferred embodiment, the recombinant expression construct is comprised of plasmid sequences derived from the plasmid pcDNAI/neo and cDNA or genomic DNA of mouse or human MSH® gene. This invention includes a recombinant expression construct comprising essentially the nucleotide sequences of genomic or cDNA clones of mouse or human MSH® in an embodiment that provides for their expression in cultures of transformed eukaryotic cells.

It is also an object of this invention to provide cultures of transformed eukaryotic cells that have been transformed with such a recombinant expression construct and that synthesize mammalian, preferably mouse or human, MSH® protein. In a preferred embodiment, the invention provides human 293 cells that synthesize mouse MSH®. In an additional preferred embodiment, the invention provides human 293 cells that synthesize human MSH® protein.

The present invention also includes protein preparations of mammalian, preferably mouse or human MSH®, and preparations of membranes containing mammalian MSH®, derived from cultures of transformed eukaryotic cells. In a preferred embodiment, cell membranes containing mouse MSH® protein are isolated from 293 cell cultures transformed with a recombinant expression construct that directs the synthesis of mouse MSH®. In another preferred embodiment, cell membranes containing human MSH® protein are isolated from 293 cell cultures transformed with a recombinant expression construct that directs the synthesis of human MSH®.

It also an object of this invention to provide mammalian, preferably mouse or human MSH® for use in the in vitro screening of novel adenosine agonist and antagonist compounds. In a preferred embodiment, membrane preparations containing the mouse MSH®, derived from cultures of transformed eukaryotic cells, are used to determine the drug dissociation properties of various novel adenosine agonist and antagonist compounds in vitro. In another preferred embodiment, membrane preparations containing the human MSH®, derived from cultures of transformed eukaryotic cells, are used to determine the drug dissociation properties of various novel adenosine agonist and antagonist compounds in vitro. These properties are then used to characterize such novel compounds by comparison to the binding properties of known mouse or human MSH® agonists and antagonists.

The present invention will also be useful for the in vivo detection of analogues of agonists or antagonists of MSH®, known or unknown, either naturally occurring or as the embodiments of a drug.

It is an object of the present invention to provide a method for the quantitative detection of agonists or antagonists, or analogues thereof, of MSH®, known or unknown, either naturally occurring or as the embodiments of a drug. It is an additional object of the invention to provide a method to detect such agonists, antagonists, or analogues thereof in blood, saliva, semen, cerebrospinal fluid, plasma, lymph, or any other bodily fluid.

Specific preferred embodiments of the present invention will become evident from the following more detailed description of certain preferred embodiments and the claims.

DETAILED DESCRIPTION OF THE PREFERRED EMBODIMENTS

The term "melanocyte stimulating hormone receptor" as used herein refers to proteins substantially homologous to, and having substantially the same biological activity as, the protein coded for by the nucleotide sequence depicted in FIG. 1 (SEQ ID NO:3). This definition is intended to encompass natural allelic variations in the melanocyte stimulating hormone receptor sequence. Cloned genes of the present invention may code for MSH®s of any species of origin, including, for example, mouse, rat, rabbit, cat, and human, but preferably code for receptors of mammalian, most preferably mouse and human, origin.

Nucleic acid hybridization probes provided by the invention comprise DNA sequences that are substantially homologous to the DNA sequences in FIG. 1A (SEQ ID NO:3) and 1B (SEQ ID NO:5). Nucleic acid probes are useful for detecting MSH® gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as the MSH® from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art.

DNA which encodes the MSH® may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MSH® gene sequence information provided herein. Probes may be labeled with a detectable group such as a fluorescent group, a radioactive atom or a chemiluminescent group in accordance with know procedures and used in conventional hybridization assays, as described in greater detail in the Examples below. In the alternative, MSH® gene sequences may be obtained by use of the polymerase chain reaction (PCR) procedure, with the PCR oligonucleotide primers being produced from the MSH® gene sequence provided herein. See U.S. Pat. Nos. 4,683,195 to Mullis et al. and 4,683,202 to Mullis.

The MSH® may be synthesized in host cells transformed with a recombinant expression construct comprising a DNA sequence encoding the MSH®. Such a recombinant expression construct can also be comprised of a vector that is a replicable DNA construct. Vectors are used herein either to amplify DNA encoding the MSH® and/or to express DNA which encodes the MSH®. For the purposes of this invention, a recombinant expression construct is a replicable DNA construct in which a DNA sequence encoding the MSH® is operably linked to suitable control sequences capable of effecting the expression of the MSH® in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNAI/neo. Transformed host cells are cells which have been transformed or transfected with recombinant expression constructs made using recombinant DNA techniques and comprising a mammalian MSH®. Transformed host cells may ordinarily express the mammalian MSH®, but host cells transformed for purposes of cloning or amplifying nucleic acid hybridization probe DNA need not express the receptor. When expressed, the mammalian MSH® will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in the same translational reading frame.

Cultures of cells derived from multicellular organisms are a desirable host for recombinant MSH® synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. Human 293 cells are preferred. Expression vectors for such cells ordinarily include (if necessary) an origin of replication, a promoter located upstream from the gene to be expressed, along with a ribosome binding site, RNA splice sites (if intron-containing genomic DNA is used), a polyadenylation site, and a transcriptional termination sequence.

An origin of replication may be provided either by construction of the vector to include an exogenous origin, such as may be derived from SV40 or other viral source (e.g., polyoma, adenovirus, VSV, or MPV), or may be provided by the host cell chromosomal replication mechanism. If the vector is integrated into the host cell chromosome, the latter may be sufficient.

The invention provides homogeneous compositions of mammalian MSH® protein produced by transformed eukaryotic cells as provided herein. Such homogeneous compositions are intended to be comprised of mammalian MSH® protein that comprises 90% of the protein in such homogenous composition.

Mammalian MSH® protein made from cloned genes in accordance with the present invention may be used for screening agonist compounds for MSH® activity, or for determining the amount of a MSH® agonist or antagonist drug in a solution (e.g., blood plasma or serum). For example, host cells may be transformed with a recombinant expression construct of the present invention, MSH® expressed in that host, the cells lysed, and the membranes from those cells used to screen compounds for MSH® binding activity. Competitive binding assays in which such procedures may be carded out are well known in the art. By selection of host cells which do not ordinarily express MSH®s, pure preparations of membranes containing MSH®s can be obtained. Further, MSH® agonists and antagonists can be identified by transforming host cells with vectors of the present invention. Membranes obtained from such cells can be used in binding studies wherein the drug dissociation activity is monitored.

The recombinant expression constructs of the present invention are useful in molecular biology to transform cells which do not ordinarily express the MSH® to thereafter express this receptor. Such cells are useful as intermediates for making cell membrane preparations useful for receptor binding assays, which are in turn useful for drug screening. Further, genes and vectors comprising the recombinant expression construct of the present invention are useful in gene therapy. For such purposes, retroviral vectors as described in U.S. Pat. No. 4,650,764 to Temin & Watanabe or U.S. Pat. No. 4,861,719 to Miller may be employed. Cloned genes of the present invention, or fragments thereof, may also be used in gene therapy carded out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing MSH receptor gene expression in tissues. For example, tissues can be probed in situ with oligonucleotide probes carrying detectable groups by conventional autoradiography techniques, as explained in greater detail in the Examples below, to investigate native expression of this receptor or pathological conditions relating thereto. Further, chromosomes can be probed to investigate the presence or absence of the MSH® gene, and potential pathological conditions related thereto, as also illustrated by the Examples below.

The invention also provides antibodies that are immunologically reactive to a mammalian MSH®. The antibodies provided by the invention can be raised in animals by inoculation with cells that express a mammalian MSH® or epitopes of a mammalian MSH® using methods well known in the art. Animals that can be used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian MSH®, or any cell or cell line that expresses a mammalian MSH® or any epitope therein as a result of molecular or genetic engineering, or that has been treated to increase the expression of a mammalian MSH® by physical, biochemical or genetic means. Preferred cells are human cells, most preferably human 293 cells that have been transformed with a recombinant expression construct comprising DNA sequences encoding a mammalian MSH® and that express the mammalian MSH® gene product.

The present invention provides monoclonal antibodies that are immunologically reactive with an epitope that is a mammalian MSH® present on the surface of mammalian cells, preferably human or mouse cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing a mammalian MSH®, including human cells, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention can also be produced by recombinant genetic methods well known to those of skill in the art, and the present invention encompasses antibodies made by such methods that are immunologically reactive with an epitope of a mammalian MSH®.

The present invention encompasses fragments of the antibody that are immunologically reactive with an epitope of a mammalian MSH®. Such fragments can be produced by any number of methods, including but not limited to proteolytic cleavage, chemical synthesis or preparation of such fragments by means of genetic engineering technology.

Primer III (sense): (SEQ ID NO:1)
GAGTCGACCTGTG(C/T)G(C/T)(C/G)AT(C/T)(A/G)CIIT(G/T)GAC(C/A)G(C/G)TAC
and Primer VI (antisense): (SEQ ID NO:2)
CAGAATTCAG(T/A)AGGGCAICCAGCAGAI(G/C)(G/A)(T/C)GAA The present invention also encompasses single-chain antibodies that are immunologically reactive with an epitope of a mammalian MSH® made by methods known to those of skill in the art.

The present invention also encompasses an epitope of a mammalian MSH® that is comprised of sequences and/or a conformation of sequences present in the mammalian MSH® molecule. This epitope may be naturally occurring, or may be the result of proteolytic cleavage of the mammalian MSH® molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of immunologically reactive light chain and heavy chain peptides to an epitope that is a mammalian MSH®. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They are set forth for explanatory purposes only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, human melanoma cDNA was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 244: 569–72; Zhou et al. 1990, Nature 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, Biochemistry 18: 5294–5299). Double-stranded cDNA was synthesized from total RNA with murine reverse transcriptase (BRL, Gaithersburg, Md.) by oligo-dT priming [Maniatis et al., *Molecular Cloning: A Laboratory Manual*, (Cold Spring Harbor Laboratory Press, Cold Spring Harbor, N.Y.), 1990]. The melanoma cDNA mixture was then subjected to 45 cycles of PCR amplification using 500 picomoles of degenerate oligonucleotide primers having the following sequence:

in 100 μl of a solution containing 50 mM Tris-HCl (pH 8.3), 2.5 mM $MgCl_2$, 0.01% gelatin, 200 μM each dNTP, and 2.5 units of Taq polymerase (Saiki et al., 1988, Science 239: 487–491). These primers were commercially synthesized by Research Genetics Inc. (Huntsville, Al.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and the insert was then cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, Proc. Natl. Acad. Sci. USA 74: 5463–5467). Two types of sequences homologous to other G-protein coupled receptors were identified.

EXAMPLE 2

Isolation and Sequence Analysis of Mouse αMSH Receptor cDNA

Probes isolated in Example 1 were used to screen a Cloudman melanoma cDNA library in order to isolate a full-length cDNA corresponding to the cloned probe. One clone was isolated from a library of $5 \times 10^6$ clones screened as described below. This clone contained an insert of 2.6 kilobases (kb). The nucleotide sequence of the complete coding region was determined, as shown in FIG. 1A (SEQ ID NO:3).

The PCR probe was labeled by the random-priming method (Stratagene PrimeIt, #300387, LaJolla, Calif.) and used to screen a Cloudman melanoma line cDNA library constructed in the λZAP vector (Stratagene). Library screening was performed using techniques well-known in the art as described in Bunzow et al. (1988, Nature 336: 783–787) at moderate stringency (40% formamide, 1M NaCl, 50 mM Tris-HCl, pH 7.5, 0.1% sodium pyrophosphate, 0.2% sodium dodecyl sulfate, 100 µg/ml salmon sperm DNA, 10X Denhardt's solution). One cDNA clone was identified (termed mmdA) and its 2.6 kb cDNA insert was isolated and subcloned into pBKS (Stratagene); the resulting plasmid was called pmmelA. Nucleotide sequence analysis and homology comparisons were done on the OHSU computer system with software provided by Intelligenetics Inc. (Mountain View, Calif.).

The nucleotide sequence of pmmelA (the cDNA clone isolated as described above) is shown in FIG. 1A (SEQ ID NO:3). The longest open reading frame of this cDNA encodes a predicted protein product of 315 amino acids with a calculated molecular weight of 35.3 kilodaltons (kD). The deduced amino acid sequence is shown in FIG. 2 (SEQ ID NO:4) as mouse MSH-R. Single letter amino acid codes are used [see, G. Zubay, *Biochemistry* (2d ed.), 1988 (MacMillen Publishing: New York) p.33]. Uppercase lettering indicates amino acid residues in common between the receptor proteins shown; lowercase lettering indicates divergent residues.

Hydrophobicity analysis (Kyte & Doolittle, 1982, J. Mol. Biol. 157: 105–132) of the deduced amino acid sequence showed that the protein contains seven hydrophobic stretches of 21 to 26 amino acids apiece. Putative transmembrane domains are overlined and designated with Roman numerals.

EXAMPLE 3

Construction of Mouse αMSH® Expression Plasmids, DNA Transfection and Functional Expression of the αMSH® Gene Product In order to biochemically characterize the putative mouse αMSH® cDNA isolated as in Example 2, and to confirm that it encodes an αMSH receptor, mmelA was cloned into a mammalian expression vector, this vector transfected into human 293 cells, and cell lines generated that expressed the putative αMSH® receptor at the cell surface. Such cells and membranes isolated from such cells were used for biochemical characterization experiments described below.

The entire coding region of the αMSH® cDNA insert from mmelA contained in a 2.1 kb fragment was excised from pBSK and subcloned into the BamHI/XhoI sites of pcDNAI/neo expression vector (Invitrogen, San Diego, Calif.). The resulting plasmid was called pcDNA-mmelA. pcDNA-mmelA plasmid DNA was prepared in large-scale through one cycle of CsCl gradient ultracentrifugation and 20 µg pcDNA-mmelA DNA were transfected into each 100 mm dish of 293 cells using the calcium phosphate method (see Chen & Okayama, 1987, Mol. Cell. Biol. 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 µg/ml; selection was started 72 hr after transfection and continued for 3 weeks.

The αMSH® is known to couple to G-proteins and thereby activate adenyl cyclase, increasing intracellular levels of cAMP (see Buckley & Ramachandran, 1981, Proc. Natl. Acad. Sci. USA 78: 7431–7435; Grahame-Smith et at., 1967, J. Biol. Chem 242: 5535–5541; Mertz & Catt, 1991, Proc. Natl. Acad. Sci. USA 88: 8525–8529; Pawalek et al., 1976, Invest. Dermatol. 66: 200–209). This property of cells expressing the αMSH receptor was used analyze expression of the αMSH receptor in cell colonies transfected with the expression vectors described herein as follows. Cells (~1× $10^6$) were plated in 6-well dishes, washed once with DMEM containing 1% bovine serum albumin (BSA) and 0.5mM IBMX (a phosphodiesterase inhibitor), then incubated for 45 minutes at 37° C. with varying concentrations of the melanotropic peptides αMSH, αMSH, γMSH, the MSH peptide analogues $Nle^4$, $D-Phe^7$-αMSH (NDP-MSH), and ACTH. Following hormone treatment, the cells were washed twice with phosphate buffered saline and intracellular cAMP extracted by lysing the cells with 1 ml of 60% ethanol. Intracellular cAMP concentrations were determined using an assay (Amersham) which measures the ability of cAMP to displace [8-$^3$H] cAMP from a high affinity cAMP binding protein (see Gilman, 1970, Proc. Natl. Acad. Sci. USA 67: 305–312).

The results of these experiments are shown in FIG. 3. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing the murine αMSH receptor responded to melanotropic peptides with a 2–3 fold elevation of intracellular cAMP, similar to levels of cAMP induced by these peptides in the Cloudman cell line (see Pawalek, 1985, Yale J. Biol. Med. 58: 571–578). The $EC_{50}$ values determined for αMSH ($2.0\times10^{-9}$M), ACTH ($8.0\times10^{-9}$M) and the superpotent MSH analogue NDP-MSH ($2.8\times10^{-11}$M) correspond closely to reported values (see Tatro et al., 1990, Cancer Res. 50: 1237–1242). As expected, the βMSH peptide had an $EC_{50}$ value comparable to αMSH$^{22}$ while γMSH had little or no activity (see Slominski et al., 1992, Life Sci. 50: 1103–1108), confirming the identity of this receptor as a melanocyte αMSH receptor.

EXAMPLE 4

Isolation and Characterization of a Human αMSH® Genomic Clone

In order to isolate a human counterpart of the murine melanocyte αMSH receptor gene, a human genomic library was screened at high stringency (50% formamide, 42° C.) using the human PCR fragments isolated as described in Example 1. Two different types of sequences were isolated, corresponding to the two PCR fragments, and were found to encode highly related G protein-coupled receptors. These genomic clones were sequenced as described in Example 2. One of these genomic clones was determined to encode an human MSH receptor (SEQ ID NO:5). The human MSH receptor has a predicted amino acid sequence (SEQ ID NO:6) that is 75% identical and colinear with the mouse αMSH receptor cDNA sequence (FIG. 2), represented as human MSH-R. The predicted molecular weight of the human MSH® is 34.7kD.

The predicted amino acid sequences of the mouse αMSH® (SEQ ID NO:4) and human MSH® (SEQ ID NO:6) are aligned in FIG. 2. These sequences define the melanocortin receptors as a novel subfamily of the G protein-coupled receptors with a number of unusual features. The melanocortin receptors are the smallest G protein-coupled receptors identified to date (297–317aa) resulting from a short amino terminal extracellular domain, a short carboxy-terminal intracellular domain, and a very small third intracellular loop. The melanocortin receptors lack several amino acid residues present in most G protein coupled receptors (see Probst et al., 1992, DNA & Cell Biol. 11: 1–20), including the proline residues in the 4th and 5th transmembrane domains, likely to introduce a bend in the alpha helical structure of the transmembrane domains and thought to be involved in the formation of the binding pocket (see Applebury & Hargrave, 1986, Vision Res. 26: 1881–1895), and one or both of the cysteine residues thought to form a disulfide bond between the first and second extracellular loops (see Dixon et al., 1987, EMBO J. 6: 3269–3275 and Karnik et al., 1988, Proc. Natl. Acad. Sci. USA 85: 8459–8463). Remarkably, the melanocortin receptors do not appear highly related to the other G protein-coupled receptors which recognize peptide ligands, such as the receptors for bombesin (see Spindel et al., 1990, Mol. Endocrinol. 4: 1956–1963) or substance K (see Masu et al., 1987, Nature 329: 836–838) but rather, are more closely related to the receptor for $\Delta^9$-tetrahydrocannabinol (see Matsuda et al., 1990, Nature 346: 561–564). The cannabinoid receptor also lacks the conserved proline in transmembrane 5 and the cysteine in the first extracellular loop necessary for disulfide bond formation. Least parsimony analysis with the receptor sequences shown in FIG. 2 suggests the cannabinoid and melanocortin receptors may be evolutionarily related and form a subfamily distinct from the peptide receptors and the amine receptors. Regardless of whether the similarities are the result of evolutionary conservation or convergence, the sequence and putative structural similarities between the melanocortin and cannabinoid receptors may be informative in the search for the endogenous cannabinoid-like ligand.

EXAMPLE 5

Tissue Distribution of αMSH Receptors

Figure 4A:
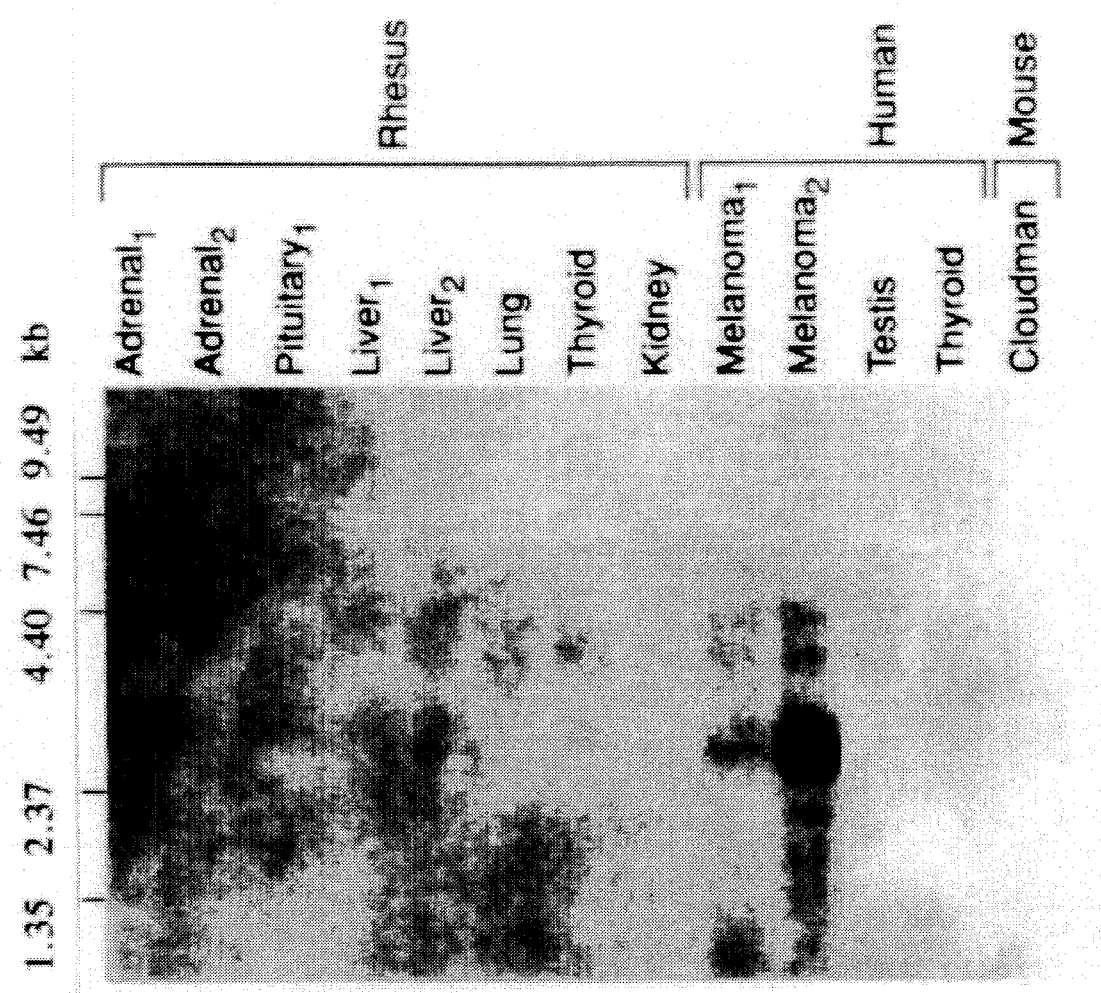
FIG. 4 illustrates the tissue distribution of human (Panel A) and mouse (Panel B) melanocyte stimulating hormone receptor gene expression by Northern blot hybridization.
Figure 4B:
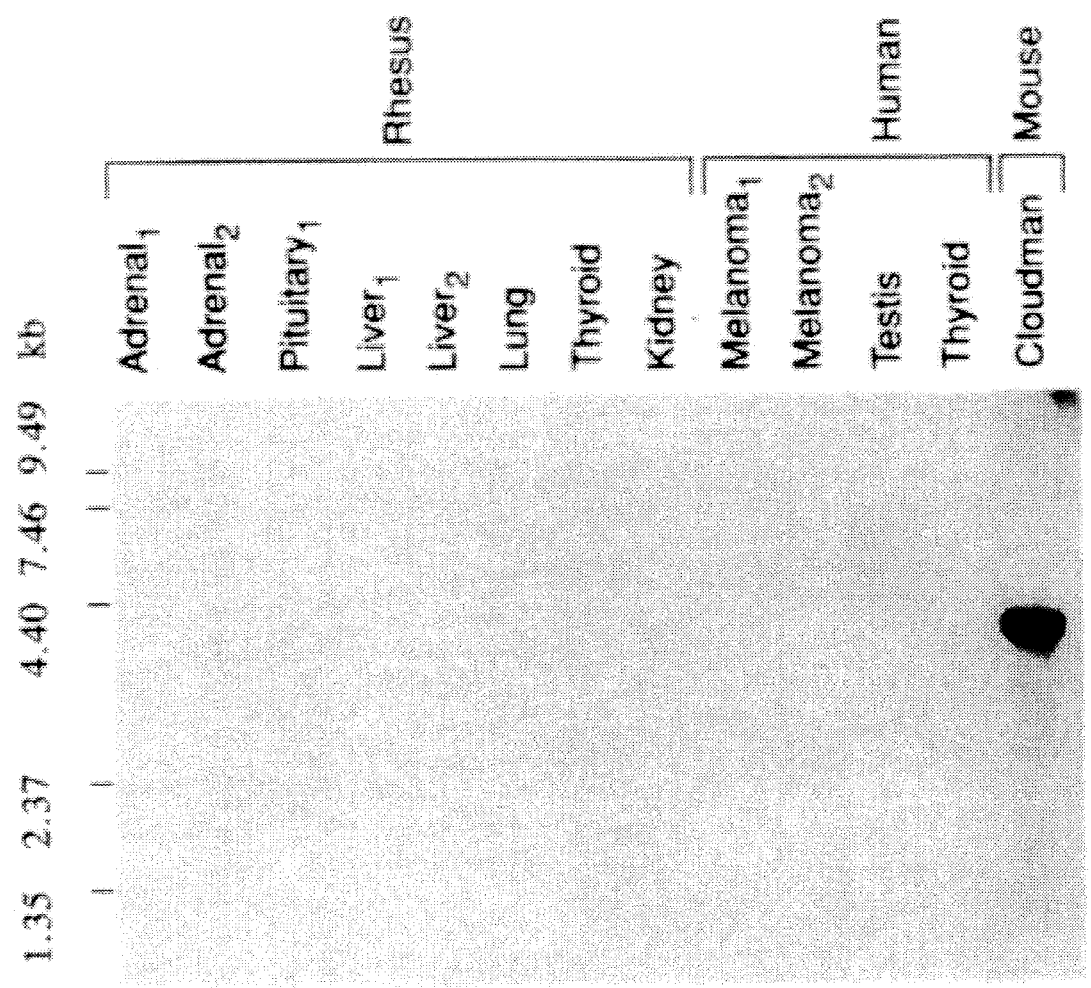

To further gain insight into these receptors, we have examined the tissue distribution of their corresponding mRNAs from various tissues by performing Northern hybridization experiments on RNA isolated from various tissues (see Maniatis et al., ibid.). The results of these experiments are shown in FIG. 4.

A panel of tissue samples was examined by Northern hybridization analysis performed under high stringency conditions. The same nitrocellulose filter was hybridized successively with a human MSH receptor probe and a mouse MSH receptor probe to determine the distribution of each receptor mRNA. The murine MSH receptor is encoded predominantly by a single mRNA species of 3.9 kb, while the human MSH receptor is encoded, in two melanoma samples, predominantly by a 3.0 kb species. High levels of receptor mRNA are seen in both primary mouse melanocytes and mouse melanoma cell lines. In contrast, extremely low levels of receptor mRNA were detected in primary human melanocytes, and many human melanoma samples (see melanoma 1, FIG. 4). Most intriguing is the dramatic elevation of MSH-R mRNA seen thus far in 3 of 11 samples tested, such as is seen in melanoma sample #2 (FIG. 4).

Additionally, we have been unable to detect expression in the brain of any of the receptors described here, despite extensive documentation of MSH binding sites there as well as in other tissues. These finding suggest the existence of alternate forms of these or related receptors that may be specifically expressed in brain tissue.

It should be understood that the foregoing disclosure emphasizes certain specific embodiments of the invention and that all modifications or alternatives equivalent thereto are within the spirit and scope of the invention as set forth in the appended claims.

---

What we claim is:

1. An isolated DNA molecule encoding a mammalian melanocyte stimulating hormone receptor, wherein the encoded melanocyte stimulating hormone receptor has a predicted isoelectric point of about 8 to about 9, a predicted molecular weight of about 34 kilodaltons, and which activates cAMP production in response to a melanotropic peptide selected from the group consisting of NDP-MSH, αMSH and ACTH.

2. An isolated DNA molecule encoding a mammalian melanocyte stimulating hormone receptor having an amino acid sequence that is the amino acid sequence identified as Sequence I.D. No. 4.

3. An isolated DNA molecule encoding a mammalian melanocyte stimulating hormone receptor that is the amino acid sequence identified as Sequence I.D. No. 6.

4. A recombinant expression construct comprising an isolated DNA molecule having a nucleotide sequence encoding the mammalian melanocyte stimulating hormone receptor of claim 2.

5. A recombinant expression construct comprising an isolated DNA molecule encoding the melanocyte stimulating hormone receptor of claim 3.

6. The recombinant expression construct of claim 4 comprising pcDNAI/neo sequences.

7. A eukaryotic cell culture transformed with the expression construct of claim 4, wherein the transformed eukaryotic cell culture is capable of expressing mouse melanocyte stimulating hormone receptor.

8. A eukaryotic cell culture transformed with the expression construct of claim 5, wherein the transformed eukaryotic cell culture is capable of expressing the human melanocyte stimulating hormone receptor.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_feature
        ( B ) LOCATION: 1..33
        ( D ) OTHER INFORMATION: /function="Degenerate
            oligonucleotide primer (sense)"

( x i ) SEQUENCE DESCRIPTION: SEQ ID NO:1:

GAGTCGACCT GTGYGYSATY RCTKGACMGS TAC         33

( 2 ) INFORMATION FOR SEQ ID NO:2:

(i) SEQUENCE CHARACTERISTICS:
    (A) LENGTH: 31 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: misc_feature
    (B) LOCATION: 1..31
    (D) OTHER INFORMATION: /function="Degenerate oligonucleotide primer (antisense)"

(xi) SEQUENCE DESCRIPTION: SEQ ID NO:2:

```
CAGAATTCAG WAGGGCACCA GCAGASRYGA A                                              31
```

(2) INFORMATION FOR SEQ ID NO:3:

(i) SEQUENCE CHARACTERISTICS:
    (A) LENGTH: 1260 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 15..959

(ix) FEATURE:
    (A) NAME/KEY: 5'UTR
    (B) LOCATION: 1..14

(ix) FEATURE:
    (A) NAME/KEY: 3'UTR
    (B) LOCATION: 960..1260

(xi) SEQUENCE DESCRIPTION: SEQ ID NO:3:

```
TTCCTGACAA GACT ATG TCC ACT CAG GAG CCC CAG AAG AGT CTT CTG GGT             50
               Met Ser Thr Gln Glu Pro Gln Lys Ser Leu Leu Gly
                1              5                  10

TCT CTC AAC TCC AAT GCC ACC TCT CAC CTT GGA CTG GCC ACC AAC CAG             98
Ser Leu Asn Ser Asn Ala Thr Ser His Leu Gly Leu Ala Thr Asn Gln
         15              20                  25

TCA GAG CCT TGG TGC CTG TAT GTG TCC ATC CCA GAT GGC CTC TTC CTC            146
Ser Glu Pro Trp Cys Leu Tyr Val Ser Ile Pro Asp Gly Leu Phe Leu
     30              35              40

AGC CTA GGG CTG GTG AGT CTG GTG GAG AAT GTG CTG GTT GTG ATA GCC            194
Ser Leu Gly Leu Val Ser Leu Val Glu Asn Val Leu Val Val Ile Ala
 45              50              55                      60

ATC ACC AAA AAC CGC AAC CTG CAC TCG CCC ATG TAT TAC TTC ATC TGC            242
Ile Thr Lys Asn Arg Asn Leu His Ser Pro Met Tyr Tyr Phe Ile Cys
                 65              70                      75

TGC CTG GCC CTG TCT GAC CTG ATG GTA AGT GTC AGC ATC GTG CTG GAG            290
Cys Leu Ala Leu Ser Asp Leu Met Val Ser Val Ser Ile Val Leu Glu
             80              85                  90

ACT ACT ATC ATC CTG CTG CTG GAG GTG GGC ATC CTG GTG GCC AGA GTG            338
Thr Thr Ile Ile Leu Leu Leu Glu Val Gly Ile Leu Val Ala Arg Val
         95              100                 105

GCT TTG GTG CAG CAG CTG GAC AAC CTC ATT GAC GTG CTC ATC TGT GGC            386
Ala Leu Val Gln Gln Leu Asp Asn Leu Ile Asp Val Leu Ile Cys Gly
     110             115                 120

TCC ATG GTG TCC AGT CTC TGC TTC CTG GGC ATC ATT GCT ATA GAC CGC            434
Ser Met Val Ser Ser Leu Cys Phe Leu Gly Ile Ile Ala Ile Asp Arg
125             130                 135                 140

TAC ATC TCC ATC TTC TAT GCG CTG CGT TAT CAC AGC ATC GTG ACG CTG            482
```

```
Tyr  Ile  Ser  Ile  Phe  Tyr  Ala  Leu  Arg  Tyr  His  Ser  Ile  Val  Thr  Leu
               145                      150                     155

CCC  AGA  GCA  CGA  CGG  GCT  GTC  GTG  GGC  ATC  TGG  ATG  GTC  AGC  ATC  GTC    530
Pro  Arg  Ala  Arg  Arg  Ala  Val  Val  Gly  Ile  Trp  Met  Val  Ser  Ile  Val
          160                      165                     170

TCC  AGC  ACC  CTC  TTT  ATC  ACC  TAC  TAC  AAG  CAC  ACA  GCC  GTT  CTG  CTC    578
Ser  Ser  Thr  Leu  Phe  Ile  Thr  Tyr  Tyr  Lys  His  Thr  Ala  Val  Leu  Leu
               175                      180                     185

TGC  CTC  GTC  ACT  TTC  TTT  CTA  GCC  ATG  CTG  GCA  CTC  ATG  GCG  ATT  CTG    626
Cys  Leu  Val  Thr  Phe  Phe  Leu  Ala  Met  Leu  Ala  Leu  Met  Ala  Ile  Leu
          190                      195                     200

TAT  GCC  CAC  ATG  TTC  ACG  AGA  GCG  TGC  CAG  CAC  GTC  CAG  GGC  ATT  GCC    674
Tyr  Ala  His  Met  Phe  Thr  Arg  Ala  Cys  Gln  His  Val  Gln  Gly  Ile  Ala
205                      210                     215                     220

CAG  CTC  CAC  AAA  AGG  CGG  CGG  TCC  ATC  CGC  CAA  GGC  TTC  TGC  CTC  AAG    722
Gln  Leu  His  Lys  Arg  Arg  Arg  Ser  Ile  Arg  Gln  Gly  Phe  Cys  Leu  Lys
               225                      230                     235

GGT  GCT  GCC  ACC  CTT  ACT  ATC  CTT  CTG  GGG  ATT  TTC  TTC  CTG  TGC  TGG    770
Gly  Ala  Ala  Thr  Leu  Thr  Ile  Leu  Leu  Gly  Ile  Phe  Phe  Leu  Cys  Trp
          240                      245                     250

GGC  CCC  TTC  TTC  CTG  CAT  CTC  TTG  CTC  ATC  GTC  CTC  TGC  CCT  CAG  CAC    818
Gly  Pro  Phe  Phe  Leu  His  Leu  Leu  Leu  Ile  Val  Leu  Cys  Pro  Gln  His
               255                      260                     265

CCC  ACC  TGC  AGC  TGC  ATC  TTC  AAG  AAC  TTC  AAC  CTC  TTC  CTC  CTC  CTC    866
Pro  Thr  Cys  Ser  Cys  Ile  Phe  Lys  Asn  Phe  Asn  Leu  Phe  Leu  Leu  Leu
          270                      275                     280

ATC  GTC  CTC  AGC  TCC  ACT  GTT  GAC  CCC  CTC  ATC  TAT  GCT  TTC  CGC  AGC    914
Ile  Val  Leu  Ser  Ser  Thr  Val  Asp  Pro  Leu  Ile  Tyr  Ala  Phe  Arg  Ser
285                      290                     295                     300

CAG  GAG  CTC  CGC  ATG  ACA  CTC  AAG  GAG  GTG  CTG  CTG  TGC  TCC  TGG          959
Gln  Glu  Leu  Arg  Met  Thr  Leu  Lys  Glu  Val  Leu  Leu  Cys  Ser  Trp
               305                      310                     315

TGATCAGAGG  GCGCTGGGCA  GAGGGTGACA  GTGATATCCA  GTGGCCTGCA  TCTGTGAGAC          1019

CACAGGTACT  CATCCCTTCC  TGATCTCCAT  TTGTCTAAGG  GTCGACAGGA  TGAGCTTTAA          1079

AATAGAAACC  CAGAGTGCCT  GGGGCCAGGA  GAAAGGGTAA  CTGTGACTGC  AGGGCTCACC          1139

CAGGGCAGCT  ACGGGAAGTG  GAGGAGACAG  GGATGGGAAC  TCTAGCCCTG  AGCAAGGGTC          1199

AGACCACAGG  CTCCTGAAGA  GCTTCACCTC  TCCCCACCTA  CAGGCAACTC  CTGCTCAAGC          1259

C                                                                              1260
```

( 2 ) INFORMATION FOR SEQ ID NO:4:

( i ) SEQUENCE CHARACTERISTICS:
        ( A ) LENGTH: 315 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Ser  Thr  Gln  Glu  Pro  Gln  Lys  Ser  Leu  Leu  Gly  Ser  Leu  Asn  Ser
  1                 5                     10                     15

Asn  Ala  Thr  Ser  His  Leu  Gly  Leu  Ala  Thr  Asn  Gln  Ser  Glu  Pro  Trp
               20                      25                     30

Cys  Leu  Tyr  Val  Ser  Ile  Pro  Asp  Gly  Leu  Phe  Leu  Ser  Leu  Gly  Leu
          35                      40                     45

Val  Ser  Leu  Val  Glu  Asn  Val  Leu  Val  Val  Ile  Ala  Ile  Thr  Lys  Asn
50                      55                     60

Arg  Asn  Leu  His  Ser  Pro  Met  Tyr  Tyr  Phe  Ile  Cys  Cys  Leu  Ala  Leu
```

|  |  |  |  | 65 |  |  |  |  | 70 |  |  |  |  | 75 |  |  |  |  | 80 |
|---|---|---|---|---|---|---|---|---|---|---|---|---|---|---|---|---|---|---|---|
| Ser | Asp | Leu | Met | Val | Ser | Val | Ser | Ile | Val | Leu | Glu | Thr | Thr | Ile | Ile |
|  |  |  |  | 85 |  |  |  |  | 90 |  |  |  |  | 95 |  |
| Leu | Leu | Leu | Glu | Val | Gly | Ile | Leu | Val | Ala | Arg | Val | Ala | Leu | Val | Gln |
|  |  |  | 100 |  |  |  |  | 105 |  |  |  |  | 110 |  |  |
| Gln | Leu | Asp | Asn | Leu | Ile | Asp | Val | Leu | Ile | Cys | Gly | Ser | Met | Val | Ser |
|  |  | 115 |  |  |  |  | 120 |  |  |  |  | 125 |  |  |  |
| Ser | Leu | Cys | Phe | Leu | Gly | Ile | Ile | Ala | Ile | Asp | Arg | Tyr | Ile | Ser | Ile |
|  | 130 |  |  |  |  | 135 |  |  |  |  | 140 |  |  |  |  |
| Phe | Tyr | Ala | Leu | Arg | Tyr | His | Ser | Ile | Val | Thr | Leu | Pro | Arg | Ala | Arg |
| 145 |  |  |  |  | 150 |  |  |  |  | 155 |  |  |  |  | 160 |
| Arg | Ala | Val | Val | Gly | Ile | Trp | Met | Val | Ser | Ile | Val | Ser | Ser | Thr | Leu |
|  |  |  |  | 165 |  |  |  |  | 170 |  |  |  |  | 175 |  |
| Phe | Ile | Thr | Tyr | Tyr | Lys | His | Thr | Ala | Val | Leu | Leu | Cys | Leu | Val | Thr |
|  |  |  | 180 |  |  |  |  | 185 |  |  |  |  | 190 |  |  |
| Phe | Phe | Leu | Ala | Met | Leu | Ala | Leu | Met | Ala | Ile | Leu | Tyr | Ala | His | Met |
|  |  | 195 |  |  |  |  | 200 |  |  |  |  | 205 |  |  |  |
| Phe | Thr | Arg | Ala | Cys | Gln | His | Val | Gln | Gly | Ile | Ala | Gln | Leu | His | Lys |
|  | 210 |  |  |  |  | 215 |  |  |  |  | 220 |  |  |  |  |
| Arg | Arg | Arg | Ser | Ile | Arg | Gln | Gly | Phe | Cys | Leu | Lys | Gly | Ala | Ala | Thr |
| 225 |  |  |  |  | 230 |  |  |  |  | 235 |  |  |  |  | 240 |
| Leu | Thr | Ile | Leu | Leu | Gly | Ile | Phe | Phe | Leu | Cys | Trp | Gly | Pro | Phe | Phe |
|  |  |  |  | 245 |  |  |  |  | 250 |  |  |  |  | 255 |  |
| Leu | His | Leu | Leu | Leu | Ile | Val | Leu | Cys | Pro | Gln | His | Pro | Thr | Cys | Ser |
|  |  |  | 260 |  |  |  |  | 265 |  |  |  |  | 270 |  |  |
| Cys | Ile | Phe | Lys | Asn | Phe | Asn | Leu | Phe | Leu | Leu | Leu | Ile | Val | Leu | Ser |
|  |  | 275 |  |  |  |  | 280 |  |  |  |  | 285 |  |  |  |
| Ser | Thr | Val | Asp | Pro | Leu | Ile | Tyr | Ala | Phe | Arg | Ser | Gln | Glu | Leu | Arg |
|  | 290 |  |  |  |  | 295 |  |  |  |  | 300 |  |  |  |  |
| Met | Thr | Leu | Lys | Glu | Val | Leu | Leu | Cys | Ser | Trp |  |  |  |  |  |
| 305 |  |  |  | 310 |  |  |  |  | 315 |  |  |  |  |  |  |

(2) INFORMATION FOR SEQ ID NO:5:

(i) SEQUENCE CHARACTERISTICS:
        (A) LENGTH: 1633 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 462..1415

(ix) FEATURE:
        (A) NAME/KEY: 5'UTR
        (B) LOCATION: 1..461

(ix) FEATURE:
        (A) NAME/KEY: 3'UTR
        (B) LOCATION: 1416..1633

(xi) SEQUENCE DESCRIPTION: SEQ ID NO:5:

| CCCGCATGTG | GCCGCCCTCA | ATGGAGGGCT | CTGAGAACGA | CTTTTAAAAC | GCAGAGAAAA | 60 |
| AGCTCCATTC | TTCCCAGACC | TCAGCGCAGC | CCTGGCCCAG | GAAGGGAGGA | GACAGAGGCC | 120 |
| AGGACGGTCC | AGAGGTGTCG | AAATGTCCTG | GGAACCTGAG | CAGCAGCCAC | CAGGGAAGAG | 180 |
| GCAGGGAGGG | AGCTGAGGAC | CAGGCTTGGT | TGTGAGAATC | CCTGAGCCCA | GGCGGTTGAT | 240 |

-continued

```
GCCAGGAGGT GTCTGGACTG GCTGGGCCAT GCCTGGGCTG ACCTGTCCAG CCAGGGAGAG     300

GGTGTGAGGG CAGATCTGGG GGTGCCCAGA TGGAAGGAGG CAGGCATGGG GACACCCAAG     360

GCCCCCTGGC AGCACCATGA ACTAAGCAGG ACACCTGGAG GGAAGAACT GTGGGGACCT      420

GGAGGCCTCC AACGACTCCT TCCTGCTTCC TGGACAGGAC T ATG GCT GTG CAG         473
                                              Met Ala Val Gln
                                               1

GGA TCC CAG AGA AGA CTT CTG GGC TCC CTC AAC TCC ACC CCC ACA GCC       521
Gly Ser Gln Arg Arg Leu Leu Gly Ser Leu Asn Ser Thr Pro Thr Ala
 5              10                  15                  20

ATC CCC CAG CTG GGG CTG GCT GCC AAC CAG ACA GGA GCC CGG TGC CTG       569
Ile Pro Gln Leu Gly Leu Ala Ala Asn Gln Thr Gly Ala Arg Cys Leu
         25                  30                  35

GAG GTG TCC ATC TCT GAC GGG CTC TTC CTC AGC CTG GGG CTG GTG AGC       617
Glu Val Ser Ile Ser Asp Gly Leu Phe Leu Ser Leu Gly Leu Val Ser
             40                  45                  50

TTG GTG GAG AAC GCG CTG GTG GTG GCC ACC ATC GCC AAG AAC CGG AAC       665
Leu Val Glu Asn Ala Leu Val Val Ala Thr Ile Ala Lys Asn Arg Asn
                 55                  60                  65

CTG CAC TCA CCC ATG TAC TGC TTC ATC TGC TGC CTG GCC TTG TCG GAC       713
Leu His Ser Pro Met Tyr Cys Phe Ile Cys Cys Leu Ala Leu Ser Asp
 70                  75                  80

CTG CTG GTG AGC GGG ACG AAC GTG CTG GAG ACG GCC GTC ATC CTC CTG       761
Leu Leu Val Ser Gly Thr Asn Val Leu Glu Thr Ala Val Ile Leu Leu
 85                  90                  95                 100

CTG GAG GCC GGT GCA CTG GTG GCC CGG GCT GCG GTG CTG CAG CAG CTG       809
Leu Glu Ala Gly Ala Leu Val Ala Arg Ala Ala Val Leu Gln Gln Leu
             105                 110                 115

GAC AAT GTC ATT GAC GTG ATC ACC TGC AGC TCC ATG CTG TCC AGC CTC       857
Asp Asn Val Ile Asp Val Ile Thr Cys Ser Ser Met Leu Ser Ser Leu
                 120                 125                 130

TGC TTC CTG GGC GCC ATC GCC GTG GAC CGC TAC ATC TCC ATC TTC TAC       905
Cys Phe Leu Gly Ala Ile Ala Val Asp Arg Tyr Ile Ser Ile Phe Tyr
         135                 140                 145

GCA CTG CGC TAC CAC AGC ATC GTG ACC CTG CCG CGG GCG CCG CGA GCC       953
Ala Leu Arg Tyr His Ser Ile Val Thr Leu Pro Arg Ala Pro Arg Ala
 150                 155                 160

GTT GCG GCC ATC TGG GTG GCC AGT GTC GTC TTC AGC ACG CTC TTC ATC      1001
Val Ala Ala Ile Trp Val Ala Ser Val Val Phe Ser Thr Leu Phe Ile
165                 170                 175                 180

GCC TAC TAC GAC CAC GTG GCC GTC CTG CTG TGC CTC GTG GTC TTC TTC      1049
Ala Tyr Tyr Asp His Val Ala Val Leu Leu Cys Leu Val Val Phe Phe
             185                 190                 195

CTG GCT ATG CTG GTG CTC ATG GCC GTG CTG TAC GTC CAC ATG CTG GCC      1097
Leu Ala Met Leu Val Leu Met Ala Val Leu Tyr Val His Met Leu Ala
             200                 205                 210

CGG GCC TGC CAG CAC GCC CAG GGC ATC GCC CGG CTC CAC AAG AGG CAG      1145
Arg Ala Cys Gln His Ala Gln Gly Ile Ala Arg Leu His Lys Arg Gln
             215                 220                 225

CGC CCG GTC CAC CAG GGC TTT GGC CTT AAA GGC GCT GTC ACC CTC ACC      1193
Arg Pro Val His Gln Gly Phe Gly Leu Lys Gly Ala Val Thr Leu Thr
         230                 235                 240

ATC CTG CTG GGC ATT TTC TTC CTC TGC TGG GGC CCC TTC TTC CTG CAT      1241
Ile Leu Leu Gly Ile Phe Phe Leu Cys Trp Gly Pro Phe Phe Leu His
245                 250                 255                 260

CTC ACA CTC ATC GTC CTC TGC CCC GAG CAC CCC ACG TGC GGC TGC ATC      1289
Leu Thr Leu Ile Val Leu Cys Pro Glu His Pro Thr Cys Gly Cys Ile
                 265                 270                 275

TTC AAG AAC TTC AAC CTC TTT CTC GCC CTC ATC ATC TGC AAT GCC ATC      1337
Phe Lys Asn Phe Asn Leu Phe Leu Ala Leu Ile Ile Cys Asn Ala Ile
```

|     |     |     |     | 280 |     |     |     | 285 |     |     |     | 290 |     |     |      |
|-----|-----|-----|-----|-----|-----|-----|-----|-----|-----|-----|-----|-----|-----|-----|------|
| ATC | GAC | CCC | CTC | ATC | TAC | GCC | TTC | CAC | AGC | CAG | GAG | CTC | CGC | AGG | ACG  | 1385
| Ile | Asp | Pro | Leu | Ile | Tyr | Ala | Phe | His | Ser | Gln | Glu | Leu | Arg | Arg | Thr  |
|     |     | 295 |     |     |     |     | 300 |     |     |     |     | 305 |     |     |      |

| CTC | AAG | GAG | GTG | CTG | ACA | TGC | TCC | TGG | TGAGCGCGGT | GCACGCGCTT | 1432
| Leu | Lys | Glu | Val | Leu | Thr | Cys | Ser | Trp |            |            |
|     | 310 |     |     |     |     | 315 |     |     |            |            |

TAAGTGTGCT GGGCAGAGGG AGGTGGTGAT ATTGTGGTCT GGTTCCTGTG TGACCCTGGG    1492

CAGTTCCTTA CCTCCCTGGT CCCCGTTTGT CAAAGAGGAT GGACTAAATG ATCTCTGAAA    1552

GTGTTGAAGC GCGGACCCTT CTGGGCAGGG AGGGGTCCTG CAAAACTCCA GGCAGGACTT    1612

CTCACCAGCA GTCGTGGGAA C    1633

( 2 ) INFORMATION FOR SEQ ID NO:6:

( i ) SEQUENCE CHARACTERISTICS:
        ( A ) LENGTH: 317 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Ala | Val | Gln | Gly | Ser | Gln | Arg | Arg | Leu | Leu | Gly | Ser | Leu | Asn | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Pro | Thr | Ala | Ile | Pro | Gln | Leu | Gly | Leu | Ala | Ala | Asn | Gln | Thr | Gly |
|     |     |     | 20  |     |     |     |     | 25  |     |     |     |     | 30  |     |     |

| Ala | Arg | Cys | Leu | Glu | Val | Ser | Ile | Ser | Asp | Gly | Leu | Phe | Leu | Ser | Leu |
|     |     | 35  |     |     |     |     | 40  |     |     |     |     | 45  |     |     |     |

| Gly | Leu | Val | Ser | Leu | Val | Glu | Asn | Ala | Leu | Val | Val | Ala | Thr | Ile | Ala |
|     | 50  |     |     |     |     | 55  |     |     |     |     | 60  |     |     |     |     |

| Lys | Asn | Arg | Asn | Leu | His | Ser | Pro | Met | Tyr | Cys | Phe | Ile | Cys | Cys | Leu |
| 65  |     |     |     |     | 70  |     |     |     |     | 75  |     |     |     |     | 80  |

| Ala | Leu | Ser | Asp | Leu | Leu | Val | Ser | Gly | Thr | Asn | Val | Leu | Glu | Thr | Ala |
|     |     |     |     | 85  |     |     |     |     | 90  |     |     |     |     | 95  |     |

| Val | Ile | Leu | Leu | Leu | Glu | Ala | Gly | Ala | Leu | Val | Ala | Arg | Ala | Ala | Val |
|     |     |     |     | 100 |     |     |     |     | 105 |     |     |     |     | 110 |     |

| Leu | Gln | Gln | Leu | Asp | Asn | Val | Ile | Asp | Val | Ile | Thr | Cys | Ser | Ser | Met |
|     |     |     | 115 |     |     |     |     | 120 |     |     |     |     | 125 |     |     |

| Leu | Ser | Ser | Leu | Cys | Phe | Leu | Gly | Ala | Ile | Ala | Val | Asp | Arg | Tyr | Ile |
|     | 130 |     |     |     |     | 135 |     |     |     |     | 140 |     |     |     |     |

| Ser | Ile | Phe | Tyr | Ala | Leu | Arg | Tyr | His | Ser | Ile | Val | Thr | Leu | Pro | Arg |
| 145 |     |     |     |     | 150 |     |     |     |     | 155 |     |     |     |     | 160 |

| Ala | Pro | Arg | Ala | Val | Ala | Ala | Ile | Trp | Val | Ala | Ser | Val | Val | Phe | Ser |
|     |     |     |     | 165 |     |     |     |     | 170 |     |     |     |     | 175 |     |

| Thr | Leu | Phe | Ile | Ala | Tyr | Tyr | Asp | His | Val | Ala | Val | Leu | Leu | Cys | Leu |
|     |     |     | 180 |     |     |     |     | 185 |     |     |     |     | 190 |     |     |

| Val | Val | Phe | Phe | Leu | Ala | Met | Leu | Val | Leu | Met | Ala | Val | Leu | Tyr | Val |
|     |     | 195 |     |     |     |     | 200 |     |     |     |     | 205 |     |     |     |

| His | Met | Leu | Ala | Arg | Ala | Cys | Gln | His | Ala | Gln | Gly | Ile | Ala | Arg | Leu |
|     | 210 |     |     |     |     | 215 |     |     |     |     | 220 |     |     |     |     |

| His | Lys | Arg | Gln | Arg | Pro | Val | His | Gln | Gly | Phe | Gly | Leu | Lys | Gly | Ala |
| 225 |     |     |     |     | 230 |     |     |     |     | 235 |     |     |     |     | 240 |

| Val | Thr | Leu | Thr | Ile | Leu | Leu | Gly | Ile | Phe | Phe | Leu | Cys | Trp | Gly | Pro |
|     |     |     |     | 245 |     |     |     |     | 250 |     |     |     |     | 255 |     |

| Phe | Phe | Leu | His | Leu | Thr | Leu | Ile | Val | Leu | Cys | Pro | Glu | His | Pro | Thr |
|     |     |     | 260 |     |     |     |     | 265 |     |     |     |     | 270 |     |     |

| | | | | | | | | | | | | | | | |
|---|---|---|---|---|---|---|---|---|---|---|---|---|---|---|---|
| Cys | Gly | Cys 275 | Ile | Phe | Lys | Asn | Phe 280 | Asn | Leu | Phe | Leu | Ala 285 | Leu | Ile | Ile |
| Cys | Asn 290 | Ala | Ile | Ile | Asp | Pro 295 | Leu | Ile | Tyr | Ala | Phe 300 | His | Ser | Gln | Glu |
| Leu 305 | Arg | Arg | Thr | Leu | Lys 310 | Glu | Val | Leu | Thr | Cys 315 | Ser | Trp | | | |